(12) United States Patent
Yoon et al.

(10) Patent No.: US 8,299,292 B2
(45) Date of Patent: Oct. 30, 2012

(54) METHOD OF PREPARING OF 60% OR MORE CIS-DI(C4-C20)ALKYL CYCLOHEXANE-1,4-DICARBOXYLATE

(75) Inventors: Kyong-jun Yoon, Daejeon (KR); Young-kyun Choi, Daejeon (KR)

(73) Assignee: Hanwha Chemical Corporation, Seoul (KR)

( * ) Notice: Subject to any disclaimer, the term of this patent is extended or adjusted under 35 U.S.C. 154(b) by 0 days.

(21) Appl. No.: 13/124,803

(22) PCT Filed: Oct. 16, 2009

(86) PCT No.: PCT/KR2009/005980
§ 371 (c)(1),
(2), (4) Date: Jul. 7, 2011

(87) PCT Pub. No.: WO2010/044638
PCT Pub. Date: Apr. 22, 2010

(65) Prior Publication Data
US 2011/0263770 A1 Oct. 27, 2011

(30) Foreign Application Priority Data

Oct. 16, 2008 (KR) .......................... 10-2008-0101629
Jul. 10, 2009 (KR) .......................... 10-2009-0063075

(51) Int. Cl.
*C07C 69/74* (2006.01)
(52) U.S. Cl. ........................................... 560/127
(58) Field of Classification Search .................. None
See application file for complete search history.

(56) References Cited

FOREIGN PATENT DOCUMENTS

JP 2003238479 * 2/2002
KR 100635396 B1 10/2006

OTHER PUBLICATIONS

Nobuo et al., Journal of Chromatographic Science, 1989, vol. 27, pp. 735-740.*
Database CAPLUS Chemical Abstracts Service, Columbus, Ohio, US; Database Accession No. 2003:671060, Abstract of JP 2003238479.*
Nobuo et al., "Selectivity of 2-(1-Pyrenyl)ethylsilylated Silica Gel in the Isomer Separation of Cyclohexane Derivatives", Journal of Chromatographic Science, Dec. 1989, pp. 735-740, vol. 27.

* cited by examiner

*Primary Examiner* — Karl J Puttlitz
(74) *Attorney, Agent, or Firm* — The Webb Law Firm

(57) ABSTRACT

Provided is a method for preparing 60% or more cis-di(C4-C20)alkyl cyclohexane-1,4-dicarboxylate which exhibits superior plasticizing property for PVC resin. Instead of a phthalate- or terephthalate-based aromatic ester derivative, 60% or more cis-dimethyl cyclohexane-1,4-dicarboxylate is used as a starting material. The 60% or more cis-dimethyl cyclohexane-1,4-dicarboxylate is subjected to transesterification with (C4-C20) primary alcohol to prepare 60% or more cis-di(C4-C20)alkyl cyclohexane-1,4-dicarboxylate. Methanol produced as a byproduct during the transesterification is removed and some of the primary alcohol, which is evaporated, is recycled. Thus prepared 60% or more cis-di (C4-C20)alkyl cyclohexane-1,4-dicarboxylate exhibits superior plasticizer characteristics, including good plasticizing efficiency for PVC resin, high absorption rate, good product transparency after gelling, less bleeding toward the surface upon long-term use, and the like.

13 Claims, 4 Drawing Sheets

|  | cis 81%, trans 19% | cis 3%, trans 97% |  |
|---|---|---|---|
| Ex. 4<br>1,4-DINCH |  |  | Comp. Ex. 4<br>1,4-DINCH |
| Ex. 5<br>1,4-DEHCH |  |  | Comp. Ex. 5<br>1,4-DEHCH |
| Ex. 6<br>1,4-DPHCH |  |  | Comp. Ex. 6<br>1,4-DPHCH |

METHOD OF PREPARING OF 60% OR MORE CIS-DI(C4-C20)ALKYL CYCLOHEXANE-1,4-DICARBOXYLATE

TECHNICAL FIELD

The present invention relates to a method for preparing 60% or more cis-di(C4-C20)alkyl cyclohexane-1,4-dicarboxylate, which exhibits superior plasticizing property for polyvinyl chloride (PVC) resin.

Further, the present invention relates to a method for preparing 60% or more cis-di(C4-C20)alkyl cyclohexane-1,4-dicarboxylate with high purity and high yield by minimizing side reactions.

That is to say, the present invention relates to a method for preparing higher alkyl cyclohexane-1,4-dicarboxylate with higher purity without side reactions by transesterifying dimethyl cyclohexane-1,4-dicarboxylate having a particular stereostructure with (C4-C20) higher alcohol, rather than using an aromatic compound such as phthalate and terephthalate derivatives as starting material, thereby maintaining the stereostructure.

More specifically, the present invention relates to a method for preparing 60% or more cis-di(C4-C20)alkyl cyclohexane-1,4-dicarboxylate without side reactions and with high purity through transesterification of 60% or more cis-dimethyl cyclohexane-1,4-dicarboxylate as starting material with one or more alcohol(s) selected from (C4-C20) primary alcohol.

BACKGROUND ART

Phthalates, e.g. dibutyl, dioctyl or diisononyl phthalate, have been very frequently used as plasticizers for plastics such as polyvinyl chloride (PVC). However, recently, health concerns about their use have been raised, and their use in toys or other products is increasingly criticized. In some countries, their use is prohibited. It is known through long-term animal studies that phthalates may induce peroxisome proliferation, which may be the cause of liver cancer, in mice and rats. Accordingly, demand on alternative plasticizers, which are safe for humans and the environment, is on the increase.

As an alternative, di(C6-C12)alkyl cyclohexanoate-based plasticizers are evaluated as an eco-friendly and safe material without toxicity. They are obtained by first preparing phthalate plasticizers or terephthalate plasticizers and then converting them to cyclohexanes through addition of hydrogens to the benzene ring of the plasticizer. However, according to the method, since the cyclohexanoate-based plasticizer is prepared by direct hydrogenation after preparing the high-molecular-weight terephthalate plasticizer having (C6-C12) alkyl groups, the hydrogenation of the benzene ring is relatively difficult due to the steric hindrance by the long high-molecular-weight aromatic chain and the high viscosity of the reaction solution. As a result, a more vigorous reaction condition is required to solve the difficulties of the hydrogenation, which increases the risk of side reactions, including the breakage of the long carbon chain, decomposition or reduction of ester groups, etc., thereby reducing product purity. Further, since it is impossible to control an isomer of the cis/trans content of the resultant cyclohexanoate, it is difficult to selectively prepare the 60% or more cis-dimethyl cyclohexane-1,4-dicarboxylate desired by the present invention.

Korean Patent No. 10-0635396 proposes a use of cyclohexane-1,3- and -1,4-dicarboxylic acid derivatives as a plastic plasticizer, and discloses a material prepared by hydrogenation of isophthalate and terephthalate, and a preparation method thereof. However, since the above-mentioned patent describes on the hydrogenation, which is performed on terephthalate, the afore-said problem remains.

DISCLOSURE

Technical Problem

After testing physical properties of 60% or more cis-di(C4-C20)alkyl cyclohexane-1,4-dicarboxylate as a plasticizer for PVC resin, the inventors of the present invention have found out that it exhibits superior plasticizing property for PVC resin. They have found out that di(C4-C20)alkyl cyclohexane-1,4-dicarboxylate shows different plasticizing property depending on the cis/trans contents. Especially, they have found out that the plasticizing effect is very superior when the cis content is 60% or more.

However, at present, cis-di(C4-C20)alkyl cyclohexane-1,4-dicarboxylate is not available in commercial scale. Through consistent researches on the preparation of 60% or more cis-di(C4-C20)alkyl cyclohexane-1,4-dicarboxylate, the inventors have developed a commercially available method for stably preparing 60% or more cis-di(C4-C20) alkyl cyclohexane-1,4-dicarboxylate without side reactions and with superior yield.

The inventors have developed a simple process of preparing 60% or more cis-di(C4-C20)alkyl cyclohexane-1,4-dicarboxylate without side reactions and with high purity by reacting 60% or more cis-dimethyl cyclohexane-1,4-dicarboxylate with a (C4-C20) primary alcohol under normal pressure, without a process of hydrogenating dialkyl terephthalate under high temperature and high pressure as an existing technique.

Accordingly, an object of the present invention is to provide a novel method for preparing 60% or more cis-di(C4-C20)alkyl cyclohexane-1,4-dicarboxylate which exhibits superior plasticizing property for PVC resin.

Technical Solution

The present invention provides a method for preparing 60% or more cis-di(C4-C20)alkyl cyclohexane-1,4-dicarboxylate by subjecting 60% or more cis-dimethyl cyclohexane-1,4-dicarboxylate as a starting material to transesterification with one or more alcohol(s) selected from (C4-C20) primary alcohol, rather than using phthalate or terephthalate derivatives as starting materials, in a reactor in the presence of a catalyst in order to prepare a di(C4-C20)alkyl ester compound of a cyclohexane structure, as shown in Scheme 1.

The methanol byproduct produced during the process may be removed after being condensed at a condenser equipped at the upper portion of the reactor. Another condenser may be equipped between the reactor and the condenser to condense some of the (C4-C20) primary alcohol, which is evaporated, and introduce it again into the reactor. A purification tower may be used instead of the condenser. A purification tower (which may or may not include an additional heat source supply system) operated with a reflux ratio of 0.1-20 may be equipped at the upper portion of the reactor, so that methanol is separated and removed from the primary alcohol at the upper portion and the purified primary alcohol is recovered and introduced again into the reactor at the lower portion.

Unless the methanol byproduct is removed at the condenser at the upper portion and the higher primary alcohol reactant is condensed between the condenser and the reactor and introduced again into the reactor, the desired di(C4-C20)

alkyl cyclohexane-1,4-dicarboxylate with high purity may not be obtained because of decreased reaction purity, and the cost for purification may increase.

[Scheme 1]

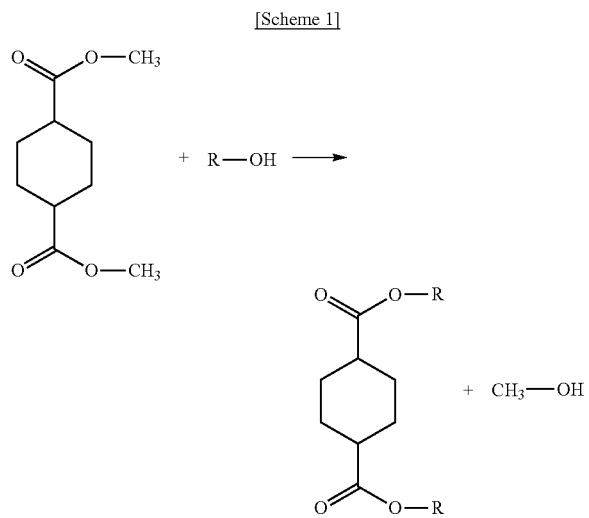

In scheme 1, R represents (C4-C20)alkyl.

The 60% or more cis-dimethyl cyclohexane-1,4-dicarboxylate which is used as a starting material in the present invention is advantageous in that no hydrogenation process is required because the benzene ring is saturated with hydrogen. The 60% or more cis-dimethyl cyclohexane-1,4-dicarboxylate may have a cis content of 60-90%, more preferably, 70-90%.

The 60% or more cis-dimethyl cyclohexane-1,4-dicarboxylate and the (C4-C20) primary alcohol are used in a molar ratio of 1:2 to 1:4. Outside the range, the primary alcohol may be evaporated during transesterification and unreacted dimethyl cyclohexane-1,4-dicarboxylate may remain. Or, a large amount of unreacted primary alcohol may remain after the reaction is completed, and it a lot of time may be required to remove them.

The (C4-C20) primary alcohol may be derived from a (C4-C20) saturated hydrocarbon. Examples may include n-butyl alcohol, isobutyl alcohol, isoheptyl alcohol, 2-ethylhexyl alcohol, isononyl alcohol, isodecyl alcohol, 2-propylheptyl alcohol, and the like, but not limited thereto.

The catalyst used in the present invention is added to facilitate the transesterification. It may be used in an amount of 0.01 to 1.0 wt %, more preferably 0.05 to 0.5 wt %, based on the 60% or more cis-dimethyl cyclohexane-1,4-dicarboxylate. If the catalyst is used in an amount less than 0.01 wt %, the reaction may not proceed well. And, an amount exceeding 1.0 wt % is uneconomical because the reaction rate and yield do not increase in proportion to the addition amount of the catalyst.

The catalyst is one capable of facilitating transesterification, and may be one or more selected from a group consisting of organometals such as tetra(C3-C10)alkyl titanate and polymers thereof, metal salts such as aluminum sulfate, lithium fluoride, potassium chloride, cesium chloride, calcium chloride, iron chloride, aluminum phosphate, potassium carbonate, etc., metal oxides such as heteropoly acid, etc., natural/synthetic zeolites, cation/anion exchange resins, and acid catalysts such as sulfuric acid, hydrochloric acid, phosphoric acid, nitric acid, p-toluenesulfonic acid, methanesulfonic acid, alkyl sulfate, etc. Among them, one or more selected from a group consisting of tetraisopropyl titanate, tetra-n-butyl titanate, tetraoctyl titanate and a mixture thereof may be preferably used.

In the present invention, the transesterification is carried out at 140 to 220° C. for 2 to 6 hours. Once the reaction begins, transesterification occurs between the 60% or more cis-dimethyl cyclohexane-1,4-dicarboxylate and the primary alcohol. During the process, methanol is produced as byproduct. The methanol byproduct needs to be removed continuously from the reactor through distillation for the reaction to proceed stably. When methanol is evaporated above a certain temperature, the primary alcohol may be evaporated together. Therefore, the primary alcohol needs to be separated from methanol and recycled to the reactor. By continuously separating the primary alcohol which is distilled along with methanol and recycling it to the reactor, the content of the primary alcohol consumed in the reaction and the reaction purity may be maintained.

In the present invention, in order to remove the methanol byproduct produced during the transesterification and to recycle the partially evaporated primary alcohol to the reactor, methanol is condensed and removed by a condenser equipped at the upper portion of the reactor and the partially evaporated primary alcohol is condensed and recycled to the reactor by another condenser equipped between the reactor and the condenser. Further, as described above, a purification tower may be used instead of the condenser. A purification tower (which may or may not include an additional heat source supply system) operated with a reflux ratio of 0.1-20 may be equipped at the upper portion of the reactor, so that methanol is separated and removed from the primary alcohol at the upper portion and the purified primary alcohol is recovered and introduced again into the reactor at the lower portion.

The reactor that may be used for the transesterification of the present invention includes a batch reactor, a mixed flow reactor, a tubular reactor, etc., but not limited thereto.

A process for preparing 60% or more cis-di(C4-C20)alkyl cyclohexane-1,4-dicarboxylate in accordance with the present invention is illustrated in FIG. 1. Referring to FIG. 1, reaction byproduct methanol ((6)) produced in a reactor ((1)) where transesterification occurs and partially evaporated primary alcohol are condensed and phase-separated by a primary condenser ((2)) maintained at an adequate temperature. Thus separated liquid primary alcohol ((7)) is recycled into the reactor and subjected to transesterification, and gaseous methanol ((8)) is transferred to a secondary condenser ((3)), where it is condensed into liquid and removed to a vessel ((11)). In case a purification tower is used instead of the condenser ((2)) in order to attain higher methanol separation efficiency, a purification tower (which may or may not include an additional heat source supply system) operated with a reflux ratio of 0.1-20 is equipped to separate methanol from the primary alcohol. Methanol is separated at the upper portion and transferred to the secondary condenser ((3)). After being condensed there, some of the methanol is recycled to the purification tower and the remaining is separated. At the lower portion of the purification tower, the purified primary alcohol is recovered and introduced again into the reactor.

Methanol boils at 64.6° C., whereas the primary alcohol used in the reaction has a much higher boiling point. For example, 2-ethylhexyl alcohol boils at 183° C. and isononyl alcohol boils at 203° C. However, within the reaction temperature range of 140-220° C., some of the primary alcohol is evaporated together with methanol. The evaporation of the primary alcohol results in a significant change of the proportion of reactants in the reactor and it becomes difficult to maintain a stable reaction. Thus, the evaporated primary alcohol ((7)) needs to be separated and recycled to the reactor. In order to effectively perform this, two condensers are equipped at the upper portion of the reactor. That is, a primary condenser is equipped at the upper portion of the reactor, and a secondary condenser is equipped to condense the gas that has passed through the primary condenser. The primary condenser condenses and separates the primary alcohol and then recycles it to the reactor. The secondary condenser condensed methanol into liquid and separates it. The primary condenser which condensed the primary alcohol is maintained at a temperature range of 70-180° C., which is higher than the boiling point of methanol and lower than the boiling point of the primary alcohol. A temperature range of 90-150° C. may be more preferable. And, the secondary condenser which needs to condense the entire amount of the gaseous methanol that has passed through the primary condenser is maintained in a temperature range of 60° C. or below, which is lower than the boiling point of methanol. A temperature range of 40° C. or lower may be more preferable.

When the transesterification continues for 2-6 hours, the reaction is completed and no more methanol is produced. When the reaction is completed, unreacted primary alcohol and catalyst remain in the reaction solution in addition to the desired 60% or more cis-di(C4-C20)alkyl cyclohexane-1,4-dicarboxylate. Therefore, a post-treatment is carried out to remove them. The reaction solution ((9)) is transferred to a post-treatment tank ((4)) for post-treatment.

The post-treatment process will be described hereinafter.

The post-treatment includes the processes of decomposition of the catalyst, removal of unreacted primary alcohol and filtration of impurities. The catalyst remaining after the completion of the transesterification, e.g. titanate-based catalyst, is decomposed into titanium oxide and saturated hydrocarbon (propane, butane, etc.) upon contact with water. Thus, a small amount of water or steam is added to the reaction solution to decompose the catalyst.

When the catalyst is completely decomposed, the reaction solution in the reactor is heated to 200° C. or above and the unreacted primary alcohol is completely removed under reduced pressure ((4)). After the unreacted primary alcohol is removed, an adsorbent is added to the reaction solution ((10)) to remove suspended impurities. Further, an alkaline adsorbent may be added to remove acidic impurities that may be produced during the reaction. Following stirring and filtration ((5)), purified, high-purity 60% or more cis-di(C4-C20)alkyl cyclohexane-1,4-dicarboxylate ((12)) may be obtained.

The alkaline adsorbent may be one or more selected from a group consisting of MgO/Cl/SO$_4$, MgO/SiO$_2$/Cl/SO$_4$, MgO/Al$_2$O$_3$/SiO$_2$/Cl/SO$_4$, MgO/Al$_2$O$_3$/SiO$_2$/CO$_2$/Cl/SO$_4$ and hydrates thereof. By using the alkaline adsorbent, it is possible to remove the acidic impurities included in the 60% or more cis-dimethyl cyclohexane-1,4-dicarboxylate used as the starting material and remaining after the completion of the reaction, and to remove such acidic substances as carboxylic acid generated from the hydrolysis of the reaction product 60% or more cis-di(C4-C20)alkyl cyclohexane-1,4-dicarboxylate by the water or steam added to decompose the catalyst.

In addition, the acidic impurities generated due to contact with water during the transesterification need to be removed through a post-treatment process. When the reaction is performed by introducing 60% or more cis-di(C4-C20)alkyl cyclohexane-1,4-dicarboxylate as the starting material, catalyst and primary alcohol even after the reactor is purged using steam and then dried, a trace amount of water remains in the reactor, which may lead to the hydrolysis of the starting material or the reaction product, thereby increasing the acid value. Therefore, the acidic impurities generated from the starting material need to be removed during the reaction or post-treatment using an alkaline adsorbent.

The 60% or more cis-di(C4-C20)alkyl cyclohexane-1,4-dicarboxylate prepared in accordance with the present invention includes di(n-butyl)cyclohexane-1,4-dicarboxylate, di(isobutyl)cyclohexane-1,4-dicarboxylate, di(isoheptyl)cyclohexane-1,4-dicarboxylate, di(2-ethylhexyl)cyclohexane-1,4-dicarboxylate, di(isononyl)cyclohexane-1,4-dicarboxylate, di(isodecyl)cyclohexane-1,4-dicarboxylate, di(2-propylheptyl)cyclohexane-1,4-dicarboxylate, etc. The di(C4-C20)alkyl cyclohexane-1,4-dicarboxylate has a cis content of 60% or more, preferably 60-90%, more preferably 70-90%.

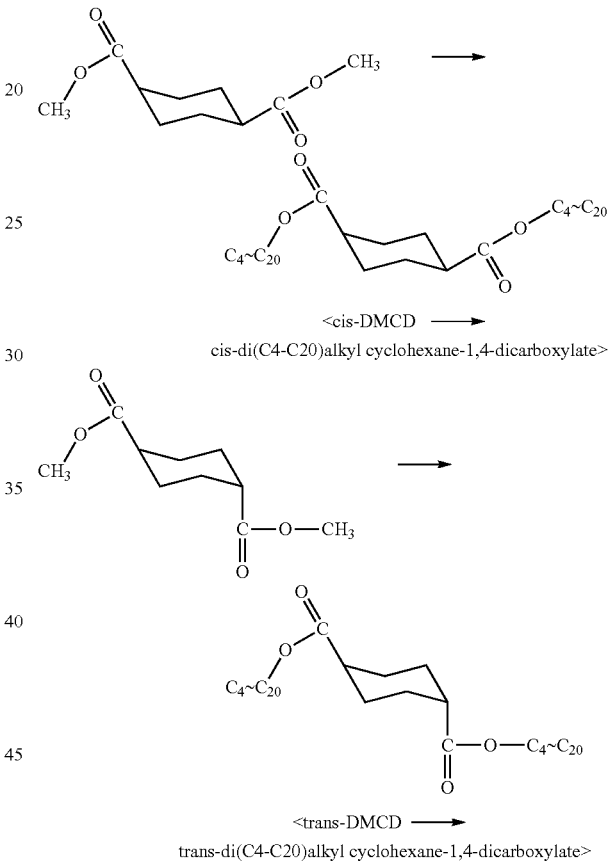

<cis-DMCD ⟶>
cis-di(C4-C20)alkyl cyclohexane-1,4-dicarboxylate>

<trans-DMCD ⟶>
trans-di(C4-C20)alkyl cyclohexane-1,4-dicarboxylate>

Advantageous Effects

Surprisingly, the 60% or more cis-di(C4-C20)alkyl cyclohexane-1,4-dicarboxylate prepared in accordance with the present invention exhibits very superior plasticizing property for PVC resin. Further, it has superior plasticizer characteristics, including fast plasticizer absorption for PVC resin, good product transparency after gelling, less bleeding toward the surface upon long-term use, and the like.

DESCRIPTION OF DRAWINGS

The above and other objects, features and advantages of the present invention will become apparent from the following description of preferred embodiments given in conjunction with the accompanying drawings, in which.

BEST MODE

Figure 1:
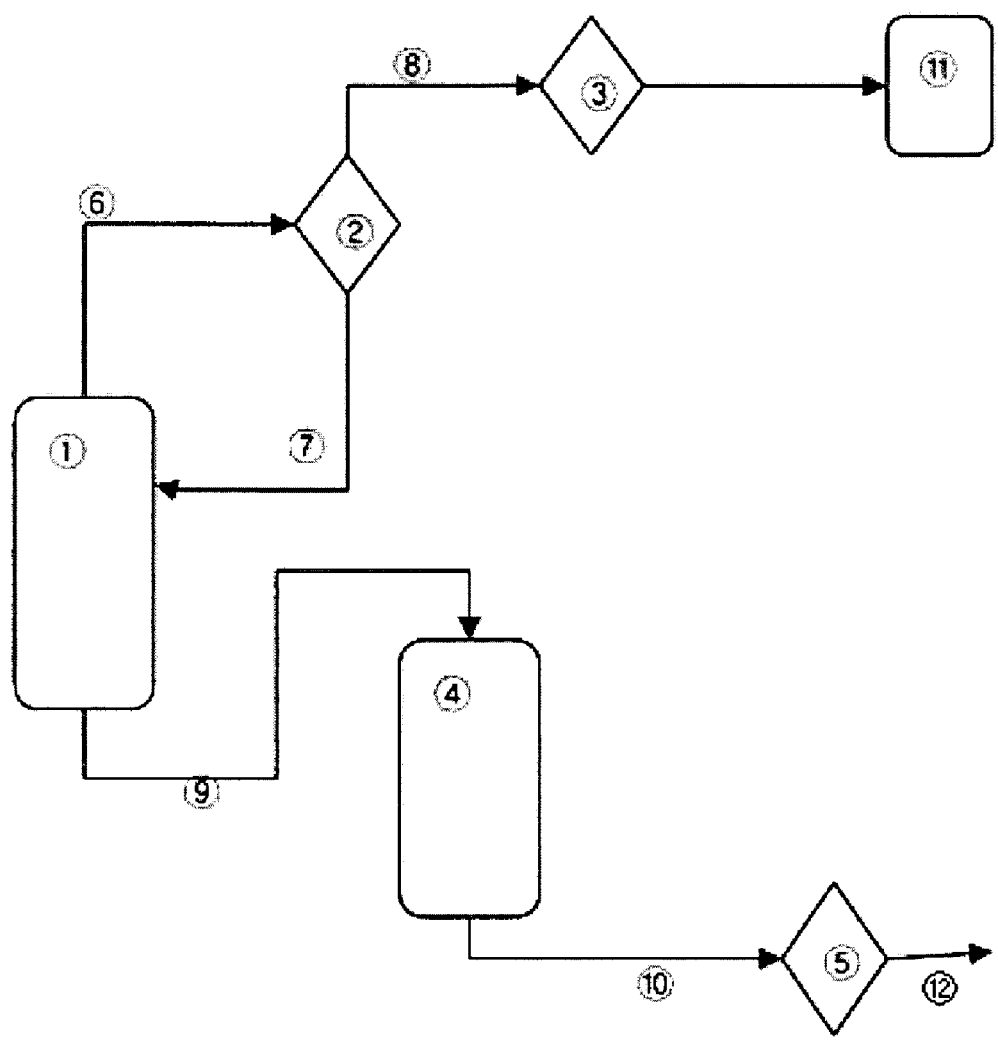
FIG. 1 schematically shows the process of transesterification.

Hereinafter, the examples and experiments will be described to help understand the present invention. The following examples and experiments are for illustrative purposes only and are not intended to limit the scope of the present invention.

Example 1

Preparation of di(isononyl)cyclohexane-1,4-dicarboxylate (1,4-DINCH)

Isononyl alcohol (8.1 mol), dimethyl cyclohexane-1,4-dicarboxylate (DMCD, cis 81.8%, trans 18.2%, SK NJC, 3.0 mol) and tetraisopropyl titanate catalyst (0.85 g) were added to a 2.5 L reactor equipped with a stirrer and two condensers and heated to 185° C. Transesterification was carried out for 6 hours under nitrogen atmosphere. Methanol, which was produced as reaction byproduct, was evaporated inside the reactor, collected as liquid while passing through the two condensers, and then removed.

Figure 2:
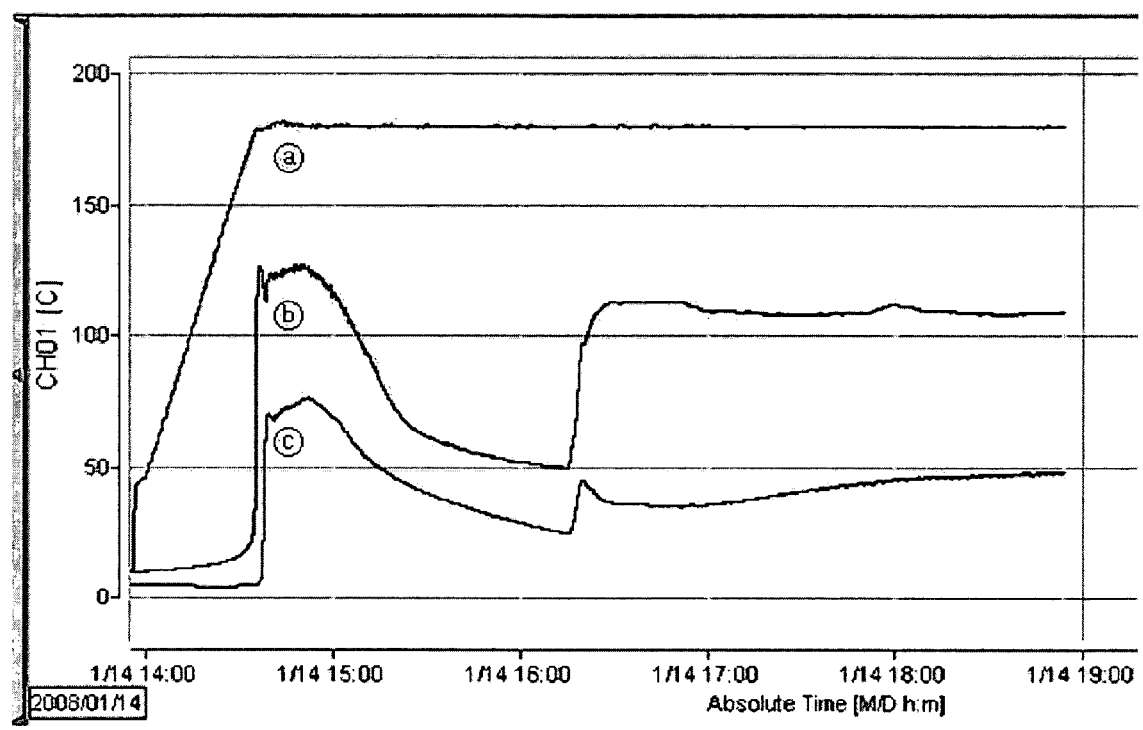
FIG. 2 is a graph showing change of temperature during transesterification (ⓐ: Temperature of reaction solution (FIG. 1 ①), ⓑ: Temperature of primary condenser (FIG. 1 ②), ⓒ: Temperature of gas introduced to secondary condenser (FIG. 1 ⑧)).
Figure 3:
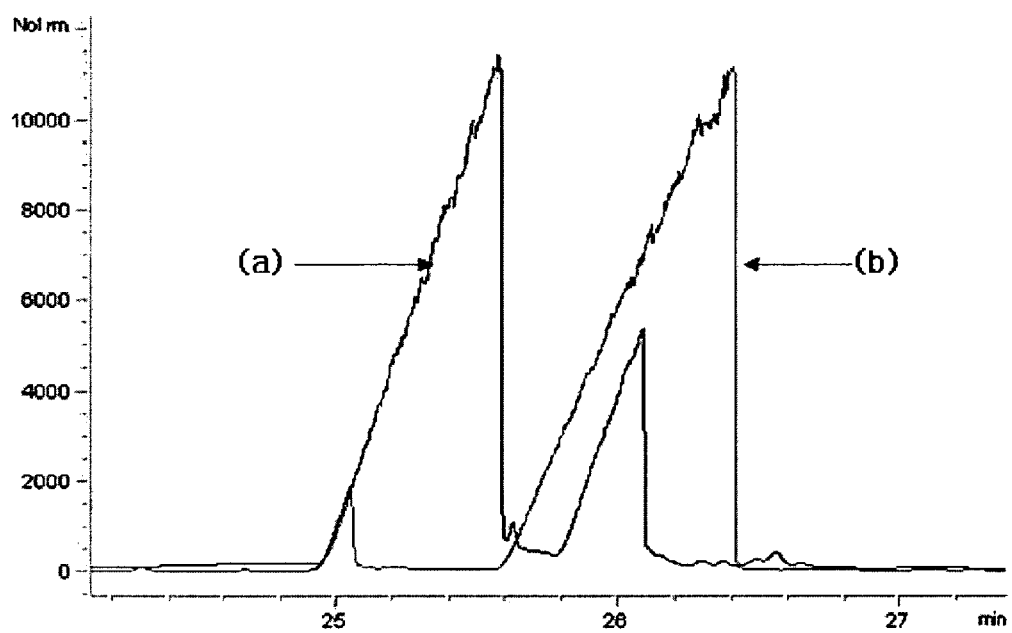
FIG. 3 shows GC analysis result of cis/trans contents of the products of Example 2 and Comparative Example 2((a)1,4-DEHCH prepared using 81% cis-DMCD, (b)1,4-DEHCH prepared using 97% trans-DMCD).

The transesterification was started when the temperature reached 185° C. As the methanol byproduct was produced, the temperatures at the primary condenser and the inlet of the secondary condenser increased rapidly [FIG. 2]. In order to reduce the loss of isononyl alcohol while methanol was removed, the temperature of the primary condenser was maintained at 150° C. or below and the temperature of the inlet of the secondary condenser was maintained at 100° C. or below.

Nitrogen was supplied to aid the removal of the methanol byproduct and block the inflow of air from outside. Nitrogen was supplied at a rate of 0.4 L/min for the first two hours following the initiation of reaction, and at a rate of 0.8 L/min thereafter.

After the reaction was completed, the reaction solution was transferred to a post-treatment tank ((④)) and cooled to 80° C. After adding deionized water (45 g), the tetraisopropyl titanate catalyst was decomposed by strong stirring for 5 minutes. After further adding activated carbon (0.45 g) and an alkaline adsorbent (Kyowaad-600, Kyowa Chemical, 0.90 g), stirring was carried out for 5 minutes. Subsequently, unreacted isononyl alcohol was removed at 200° C. under reduced pressure using a vacuum pump. The reaction product was cooled to 120° C. and filtered. Di(isononyl)cyclohexane-1,4-dicarboxylate (cis 81%, trans 19%) was obtained with a purity of 99.2%.

Example 2

Preparation of di(2-ethylhexyl)cyclohexane-1,4-dicarboxylate (1,4-DEHCH)

2-Ethylhexyl alcohol (8.1 mol), dimethyl cyclohexane-1,4-dicarboxylate (DMCD, cis 81.8%, trans 18.2%, SK NJC, 3.0 mol) and tetraisopropyl titanate catalyst (0.85 g) were added to a 2.5 L reactor equipped with a stirrer and two condensers and heated to 180° C. Di(2-ethylhexyl)cyclohexane-1,4-dicarboxylate (cis 81%, trans 19%) was obtained with a purity of 99.3% in the same manner as in Example 1.

Example 3

Preparation of di(2-propylheptyl)cyclohexane-1,4-dicarboxylate (1,4-DPHCH)

2-Propylheptyl alcohol (8.1 mol), dimethylcyclohexane-1,4-dicarboxylate (DMCD, cis 81.8%, trans 18.2%, SK NJC, 3.0 mol) and tetraisopropyl titanate catalyst (0.85 g) were added to a 2.5 L reactor equipped with a stirrer and two condensers and heated to 185° C. Di(2-propylheptyl)cyclohexane-1,4-dicarboxylate (cis 81%, trans 19%) was obtained with a purity of 99.3% in the same manner as in Example 1.

Comparative Example 1

Preparation of di(isononyl)cyclohexane-1,4-dicarboxylate

Isononyl alcohol (8.1 mol), dimethylcyclohexane-1,4-dicarboxylate (DMCD, cis 1.7%, trans 98.3%, Eastman, 3.0 mol) and tetraisopropyl titanate catalyst (0.85 g) were added to a 2.5 L reactor equipped with a stirrer and two condensers and heated to 185° C. Di(isononyl)cyclohexane-1,4-dicarboxylate (cis 3%, trans 97%) was obtained with a purity of 99.7% in the same manner as in Example 1.

Comparative Example 2

Preparation of di(2-ethylhexyl)cyclohexane-1,4-dicarboxylate

2-Ethylhexyl alcohol (8.1 mol), dimethylcyclohexane-1,4-dicarboxylate (DMCD, cis 1.7%, trans 98.3%, Eastman, 3.0 mol) and tetraisopropyl titanate catalyst (0.85 g) were added to a 2.5 L reactor equipped with a stirrer and two condensers and heated to 180° C. Di(2-ethylhexyl)cyclohexane-1,4-dicarboxylate (cis 3%, trans 97%) was obtained with a purity of 99.8% in the same manner as in Example 1.

Comparative Example 3

Preparation of di(2-propylheptyl)cyclohexane-1,4-dicarboxylate

2-Propylheptyl alcohol (8.1 mol), dimethylcyclohexane-1,4-dicarboxylate (DMCD, cis 1.7%, trans 98.3%, Eastman, 3.0 mol) and tetraisopropyl titanate catalyst (0.85 g) were added to a 2.5 L reactor equipped with a stirrer and two condensers and heated to 185° C. Di(2-propylheptyl)cyclohexane-1,4-dicarboxylate (cis 3%, trans 97%) was obtained with a purity of 99.8% in the same manner as in Example 1.

For the 60% or more cis-di(C4-C20)alkyl cyclohexane-1,4-dicarboxylate derivatives prepared in accordance with the present invention, a faster absorption rate in polyvinyl chloride (PVC) resin is preferred because the time required for mixing with PVC can be reduced. Viscosity and absorption rate in PVC resin of the di(C4-C20)alkyl cyclohexane-1,4-dicarboxylate derivatives prepared in Examples 1 to 3 and Comparative Examples 1 to 3 depending on cis/trans contents are summarized in Table 1. The plasticizer absorption rate was evaluated by comparatively measuring the times required for the plasticizer to be completely absorbed in PVC resin (P-1000, Hanwha Chemical). A planetary mixer (Brabender) was used for the measurement. After adding 400 g of P-1000 resin in the mixer maintained at 80° C., the resin temperature was uniformly increased to 80° C. while stirring. Subsequently, 50 phr of the plasticizer was added to the resin, which was being stirred. With the addition of the plasticizer, the load of the mixer blade increases. However, as the plasticizer is absorbed, the powder fluidity increases and the load decreases gradually. The plasticizer absorption rate was evaluated by measuring the time ranging from the point where the load began to increase to the point where it decreased.

TABLE 1

| Examples | Cis 81%, trans 19% | | Comparative Examples | Cis 3%, trans 97% | |
|---|---|---|---|---|---|
| | Viscosity (25° C.) | Absorption rate in PVC resin | | Viscosity (25° C.) | Absorption rate in PVC resin |
| 1,4-DINCH (Ex. 1) | 40 cP | 412 sec | 1,4-DINCH (Comp. Ex. 1) | 43 cP | 648 sec |
| 1,4-DEHCH (Ex. 2) | 28 cP | 270 sec | 1,4-DEHGH (Comp. Ex. 2) | 30 cP | 338 sec |
| 1,4-DPHCH (Ex. 3) | 44 cP | 782 sec | 1,4-DPHCH (Comp. Ex. 3) | 48 cP | 836 sec |

As seen in Table 1, the higher the cis content was, the lower the viscosity was and the faster the absorption rate in PVC resin was. That is, the high-cis plasticizer according to the present invention exhibits very superior processability and absorption rate in PVC resin.

Examples 4-6 and Comparative Examples 4-6

Comparison of performance as Plasticizer (I)<

In order to compare the performance of di(C4-C20)alkyl cyclohexane-1,4-dicarboxylate derivatives prepared in accordance with the present invention as plasticizer depending on cis/trans contents, PVC blends were prepared with the compositions and mixing proportions presented in Table 2. 0.8 mm sheets were formed by uniformly mixing in a mixing roll maintained at 160° C. for 4 minutes. Thus prepared three sheets were stacked and pressed for 10 minutes using a press forming machine at 180° C. 2 mm-thick, transparent, soft PVC sheets were obtained.

TABLE 2

| | | | Ex. 4 | Ex. 5 | Ex. 6 | Comp. Ex. 4 | Comp. Ex. 5 | Comp. Ex. 6 |
|---|---|---|---|---|---|---|---|---|
| (Unit: parts by weight) | | | | | | | | |
| PVC resin (P-1000) | | | 100 | 100 | 100 | 100 | 100 | 100 |
| Plasticizer | cis 81%, trans 19% | 1,4-DINCH (Ex. 1) | 50 | — | — | — | — | — |
| | | 1,4-DEHCH (Ex. 2) | — | 50 | — | — | — | — |
| | | 1,4-DPHCH (Ex. 3) | — | — | 50 | — | — | — |
| | cis 3%, trans 97% | 1,4-DINCH (Comp. Ex. 1) | — | — | — | 50 | — | — |
| | | 1,4-DEHCH (Comp. Ex. 2) | — | — | — | — | 50 | — |
| | | 1,4-DPHCH (Comp. Ex. 3) | — | — | — | — | — | 50 |
| KBZ-290G | | | 2.5 | 2.5 | 2.5 | 2.5 | 2.5 | 2.5 |
| E-700 | | | 2.0 | 2.0 | 2.0 | 2.0 | 2.0 | 2.0 |

※ P-1000: PVC resin (Hanwha Chemical)
※ KBZ-290G: Ba/Zn-based PVC stabilizer (Kolon Petrochemical)
※ E-700: Epoxylated soybean oil stabilizer (Songwon Industrial)

Figure 4:
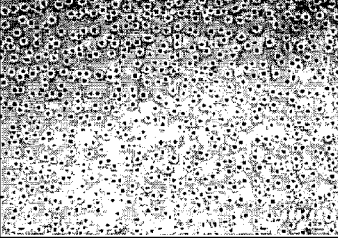
FIG. 4 shows the change of the surface of the sheets of Examples 4-6 and Comparative Examples 4-6 kept at 80° C. for 10 days.
Figure 4:
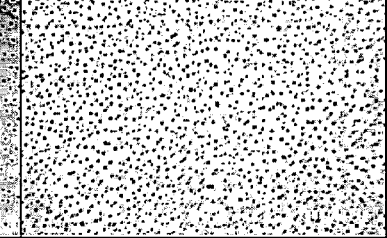
Figure 4:
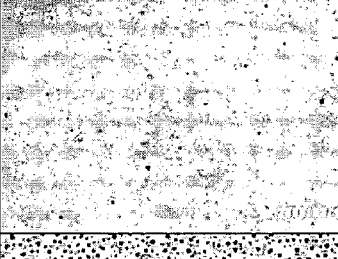
Figure 4:
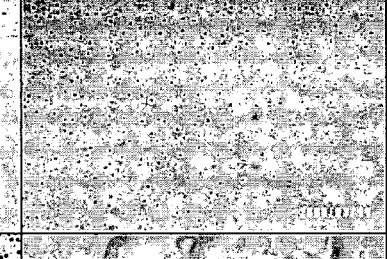
Figure 4:
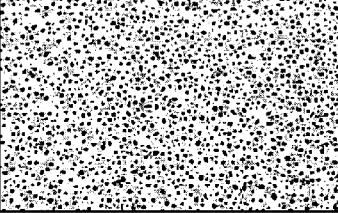
Figure 4:

In order to compare the degree of effluence of the plasticizer to the sheet surface, the transparent sheets obtained above were kept at 80° C. for 10 days and the sheet surface was observed using a microscope. As seen in FIG. 4, staining due to the effluence of the plasticizer to the sheet surface was severer as the number of carbon atoms of the primary alcohol increased (C8<C9<C10). The degree of effluence was much severer in high-trans sheets (Comparative Examples 4, 5 and 6) than in the high-cis sheets (Examples 4, 5 and 6). Particularly, the difference was larger as the number of carbon atoms increased.

For soft PVC products including a plasticizer to maintain appropriate properties and qualities for a long period of time, they should have good durability with no quality change and plasticizer effluence under various use environments. It was confirmed that high-cis plasticizers are more adequate than high-trans plasticizers, in this regard.

The change of bleeding at the sheet surface of the PVC sheets of Examples 4-6 and Comparative Examples 4-6 depending on cis/trans contents was measured by light transmittance and haze. Light transmittance and haze were measured using Haze-Gard Plus (BYK Gardner).

The PVC sheets prepared in Examples 4-6 and Comparative Examples 4-6 were kept at 80° C. for 10 days, and the change of light transmittance and haze was measured. The result is given in Table 3.

The softness of the PVC sheets of Examples 4-6 and Comparative Examples 4-6 was measured using a durometer. The higher the plasticizing effect of the plasticizer for PVC resin, the softer is the sheet and the lower the hardness. The hardness of the sheet was measured based on the Shore A scale. The result is given in Table 4. For the same di(C4-C20)alkyl cyclohexane-1,4-dicarboxylate derivatives, the high-cis derivatives (Examples 4-6) exhibited a plasticizing effect 1.7-4.5% better than the high-trans derivatives (Comparative Examples 4-6). A better plasticizing effect provides advantages in use because the same softness can be obtained with less amount.

TABLE 4

Hardness (Shore A) of PVC samples depending on cis/trans contents

| Examples | | Ex. 4 | Ex. 5 | Ex. 6 |
| --- | --- | --- | --- | --- |
| cis 81%, trans 19% | | 1,4-DINCH 85.5 | 1,4-DEHCH 82.0 | 1,4-DPHCH 87.5 |
| Comparative Examples | | Comp. Ex. 4 | Comp. Ex. 5 | Comp. Ex. 6 |
| cis 3%, trans 97% | | 1,4-DINCH 89.5 | 1,4-DEHCH 84.5 | 1,4-DPHCH 89.0 |
| Difference of hardness | | 4.5% | 3.0% | 1.7% |

TABLE 3

| | | Plasticizer | | | | | |
| --- | --- | --- | --- | --- | --- | --- | --- |
| | | cis 81%, trans 19% | | | cis 3%, trans 97% | | |
| Sheet | | 1,4-DINCH Ex. 4 | 1,4-DEHCH Ex. 5 | 1,4-DPHCH Ex. 6 | 1,4-DINCH Comp. Ex. 4 | 1,4-DEHCH Comp. Ex. 5 | 1,4-DPHCH Comp. Ex. 6 |
| Light transmittance (%) | Before | 92.3 | 92.8 | 91.8 | 92.2 | 92.7 | 90.5 |
| | After | 81.1 | 83.7 | 76.0 | 78.6 | 81.9 | 71.9 |
| Haze (%) | Before | 0.77 | 0.56 | 1.36 | 0.77 | 0.65 | 2.86 |
| | After | 2.65 | 1.38 | 7.87 | 11.00 | 1.71 | 5.17 |

As seen in Table 3, the higher the cis content, the higher is the light transmittance and the lower the haze. Before heat treatment, the light transmittance of the transparent sheet was similar (91-92%) without regard to the primary alcohol or the cis/trans contents of the cyclohexane-1,4-dicarboxylate derivatives. The haze of the sheet was also in the range from 0.5 to 2.9%. After the treatment at 80° C. for 10 days, the light transmittance of the high-cis samples (Examples 4-6) decreased to 76-84%, whereas that of the high-trans samples (Comparative Examples 4-6) decreased more to 72-82%. The change of haze showed a similar pattern to that of the light transmittance. Especially, Comparative Example 6 showed a low haze of 5.17%, which was due to the formation of an oily film on the sheet surface caused by the bleeding of the plasticizer.

Examples 7-9 and Comparative Examples 7-9

Comparison of Performance as Plasticizer (II)

In order to compare the performance of the di(C4-C20) alkyl cyclohexane-1,4-dicarboxylate derivatives prepared in accordance with the present invention as plasticizer for paste PVC resin depending on cis/trans contents, PVC resin and additives were mixed as in Table 5. Physical properties, gelling property and foaming property of the resultant paste sols were compared in Table 6.

TABLE 5

| Composition | | | Ex. 7 | Ex. 8 | Ex. 9 | Comp. Ex. 7 | Comp. Ex. 8 | Comp. Ex. 9 |
| --- | --- | --- | --- | --- | --- | --- | --- | --- |
| Paste resin (EL-103) | | | 100 | 100 | 100 | 100 | 100 | 100 |
| Plasticizer | cis 81%, trans 19% | 1,4-DINCH (Ex. 1) | 70 | — | — | — | — | — |
| | | 1,4-DEHCH (Ex. 2) | — | 70 | — | — | — | — |
| | | 1,4-DPHCH (Ex. 3) | — | — | 70 | — | — | — |

TABLE 5-continued

| Composition | | Ex. 7 | Ex. 8 | Ex. 9 | Comp. Ex. 7 | Comp. Ex. 8 | Comp. Ex. 9 |
|---|---|---|---|---|---|---|---|
| cis 3%, trans 97% | 1,4-DINCH (Comp. Ex. 1) | — | — | — | 70 | — | — |
| | 1,4-DEHCH (Comp. Ex. 2) | — | — | — | — | 70 | — |
| | 1,4-DPHCH (Comp. Ex. 3) | — | — | — | — | — | 70 |
| CNA070 | | 3.0 | 3.0 | 3.0 | 3.0 | 3.0 | 3.0 |
| DWPX03MB | | 2.0 | 2.0 | 2.0 | 2.0 | 2.0 | 2.0 |
| TiO$_2$ | | 10 | 10 | 10 | 10 | 10 | 10 |
| OM-10 | | 90 | 90 | 90 | 90 | 90 | 90 |
| BYK-5110 | | 3.0 | 3.0 | 3.0 | 3.0 | 3.0 | 3.0 |

※ CNA070: Na/Zn-based PVC stabilizer (CNA)
※ DWPX03MB: ADCA-based foaming agent (Dongjin Semichem)
※ OM-10: Calcium carbonate (Omiya Korea)
※ BYK-5110: Viscosity reducing agent (BYK)

TABLE 6

| | Plasticizer | | | | | |
|---|---|---|---|---|---|---|
| | cis 81%, trans 19% | | | cis 3%, trans 97% | | |
| Sheet | 1,4-DINCH Ex. 7 | 1,4-DEHCH Ex. 8 | 1,4-DPHCH Ex. 9 | 1,4-DINCH Comp. Ex. 7 | 1,4-DEHCH Comp. Ex. 8 | 1,4-DPHCH Comp. Ex. 9 |
| Sol viscosity | 3,850 | 3,450 | 3,700 | 4,350 | 3,500 | 4,300 |
| Gelling property | Δ | ○ | Δ | Δ | ○ | Δ |
| Foaming property | Δ | ○ | Δ | Δ | ○ | Δ |

※ ○: good, Δ; moderate, X: poor

The paste sols prepared using high-cis plasticizers (Examples 7-9) had a lower viscosity than the sols prepared using high-trans plasticizers (Comparative Examples 7-9). Thus, they exhibited better forming workability, processability, and the like. Gelling property and foaming property were comparable.

The present application contains subject matter related to Korean Patent Application Nos. 10-2008-0101629 and 10-2009-0063075, filed in the Korean Intellectual Property Office on Oct. 16, 2008 and Jul. 10, 2009, the entire contents of which are incorporated herein by reference.

While the present invention has been described with respect to the specific embodiments, it will be apparent to those skilled in the art that various changes and modifications may be made without departing from the spirit and scope of the invention as defined in the following claims.

INDUSTRIAL APPLICABILITY

The method for preparing 60% or more cis-di(C4-C20) alkyl cyclohexane-1,4-dicarboxylate according to the present invention is economical because no hydrogenation process is required. The methanol byproduct produced during the transesterification can be easily removed because it has a low boiling point. The reaction proceeds fast, and no neutralization treatment is required for removal of unreacted materials after completion of the reaction. Since the side reactions are prevented, the product can be obtained with high purity. In addition, since a post-treatment process is simply performed by filtering off impurities by adsorption without generation of waste water, the process is environment-friendly. Therefore, highly pure 60% or more cis-di(C4-C20)alkyl cyclohexane-1,4-dicarboxylate can be prepared through a simple and commercial-scale process. Further, the recovered methanol can be recycled for the preparation of 60% or more cis-dimethyl cyclohexane-1,4-dicarboxylate or for other purposes through a simple purification process.

The invention claimed is:

1. A method for preparing 60% or more cis-di(C4-C20) alkyl cyclohexane-1,4-dicarboxylate comprising subjecting 60% or more cis-dimethyl cyclohexane-1,4-dicarboxylate to transesterification with one or more alcohol(s) selected from (C4-C20) primary alcohol in a reactor in the presence of a catalyst.

2. The method according to claim 1, wherein methanol produced as a byproduct during the transesterification is condensed by a condenser or a purification tower equipped at an upper portion of the reactor and then removed, and some of the primary alcohol, which is evaporated, is condensed by another condenser or purification tower equipped between the reactor and the condenser or purification tower and recycled into the reactor.

3. The method according to claim 1, wherein the 60% or more cis-dimethyl cyclohexane-1,4-dicarboxylate and the (C4-C20) primary alcohol are used in a molar ratio of 1:2 to 1:4.

4. The method according to claim 1, wherein the catalyst is used in an amount of 0.01 to 1.0 wt % based on the 60% or more cis-dimethyl cyclohexane-1,4-dicarboxylate.

5. The method according to claim 3, wherein the (C4-C20) primary alcohol is selected from n-butyl alcohol, isobutyl alcohol, isoheptyl alcohol, 2-ethylhexyl alcohol, isononyl alcohol, isodecyl alcohol or 2-propylheptyl alcohol.

6. The method according to claim 4, wherein the catalyst is one or more selected from a group consisting of tetraisopropyl titanate, tetra-n-butyl titanate, tetraoctyl titanate and a mixture thereof.

7. The method according to claim 1, further comprising decomposing the catalyst by adding water or steam following the completion of the transesterification.

8. The method according to claim 7, further comprising removing unreacted primary alcohol by increasing the temperature inside the reactor to 140° or above.

9. The method according to claim 8, further comprising removing suspended impurities by adding an adsorbent in the reactor.

10. The method according to claim 9, further comprising removing acidic impurities by adding an alkaline adsorbent.

11. The method according to claim 10, wherein the alkaline adsorbent is one or more selected from a group consisting of $MgO/Cl/SO_4$, $MgO/SiO_2/Cl/SO_4$, $MgO/Al_2O_3/SiO_2/Cl/SO_4$, $MgO/Al_2O_3/SiO_2/CO_2/Cl/SO_4$ and hydrates thereof.

12. The method according to claim 7, wherein the prepared 60% or more cis-di(C4-C20)alkyl cyclohexane-1,4-dicarboxylate is di(n-butyl)cyclohexane-1,4-dicarboxylate, di(isobutyl)cyclohexane-1,4-dicarboxylate, di(isoheptyl)cyclohexane-1,4-dicarboxylate, di(2-ethylhexyl)cyclohexane-1,4-dicarboxylate, di(isononyl)cyclohexane-1,4-dicarboxylate, di(isodecyl)cyclohexane-1,4-dicarboxylate or di(2-propylheptyl)cyclohexane-1,4-dicarboxylate.

13. The method according to claim 10, wherein the prepared 60% or more cis-di(C4-C20)alkyl cyclohexane-1,4-dicarboxylate is di(n-butyl)cyclohexane-1,4-dicarboxylate, di(isobutyl)cyclohexane-1,4-dicarboxylate, di(isoheptyl)cyclohexane-1,4-dicarboxylate, di(2-ethylhexyl)cyclohexane-1,4-dicarboxylate, di(isononyl)cyclohexane-1,4-dicarboxylate, di(isodecyl)cyclohexane-1,4-dicarboxylate or di(2-propylheptyl)cyclohexane-1,4-dicarboxylate.

* * * * *

UNITED STATES PATENT AND TRADEMARK OFFICE
CERTIFICATE OF CORRECTION

PATENT NO.        : 8,299,292 B2                                      Page 1 of 5
APPLICATION NO.   : 13/124803
DATED             : October 30, 2012
INVENTOR(S)       : Kyong-jun Yoon et al.

It is certified that error appears in the above-identified patent and that said Letters Patent is hereby corrected as shown below:

In the Drawings

Delete Drawing Sheet 4, and replace with Drawing Sheet 4. (Attached)

In the Specifications

Column 7, Lines 9-10, delete "1,4-DEHCH" and
insert -- di (2-ethylhexyl)cyclohexane-1,4-dicarboxylate --

Column 7, Line 10, delete "1,4-DEHCH" and
insert -- di (2-ethylhexyl)cyclohexane-1,4-dicarboxylate --

Column 7, Line 30, delete "(1,4-DINCH)"

Column 8, Line 5, delete "(1,4-DEHCH)"

Column 8, Line 20, delete "(1,4-DPHCH)"

Column 10, Line 18, TABLE 1, delete "1,4-DINCH" and
insert -- di (isononyl)cyclohexane-1,4-dicarboxylate --

Column 10, Line 18, TABLE 1, delete "1,4-DINCH" and
insert -- di (isononyl)cyclohexane-1,4-dicarboxylate --

Column 10, Line 20, TABLE 1, delete "1,4-DEHCH" and
insert -- di (2-ethylhexyl)cyclohexane-1,4-dicarboxylate --

Column 10, Line 20, TABLE 1, delete "1,4-DEHCH" and
insert -- di (2-ethylhexyl)cyclohexane-1,4-dicarboxylate --

Signed and Sealed this
Second Day of July, 2013

Teresa Stanek Rea
*Acting Director of the United States Patent and Trademark Office*

Column 10, Line 22, TABLE 1, delete "1,4-DPHCH" and insert -- di (2-propylheptyl)cyclohexane-1,4-dicarboxylate --

Column 10, Line 22, TABLE 1, delete "1,4-DPHCH" and insert -- di (2-propylheptyl)cyclohexane-1,4-dicarboxylate --

Column 10, Line 53, TABLE 2, delete "1,4-DINCH" and insert -- di (isononyl)cyclohexane-1,4-dicarboxylate --

Column 10, Line 55, TABLE 2, delete "1,4-DEHCH" and insert -- di (2-ethylhexyl)cyclohexane-1,4-dicarboxylate --

Column 10, Line 57, TABLE 2, delete "1,4-DPHCH" and insert -- di (2-propylheptyl)cyclohexane-1,4-dicarboxylate --

Column 10, Line 59, TABLE 2, delete "1,4-DINCH" and insert -- di (isononyl)cyclohexane-1,4-dicarboxylate --

Column 10, Line 61, TABLE 2, delete "1,4-DEHCH" and insert -- di (2-ethylhexyl)cyclohexane-1,4-dicarboxylate --

Column 10, Line 63, TABLE 2, delete "1,4-DPHCH" and insert -- di (2-propylheptyl)cyclohexane-1,4-dicarboxylate --

Column 11, Line 32, TABLE 3, delete "1,4-DINCH" and insert -- di (isononyl)cyclohexane-1,4-dicarboxylate --

Column 11, Line 32, TABLE 3, delete "1,4-DEHCH" and insert -- di (2-ethylhexyl)cyclohexane-1,4-dicarboxylate --

Column 11, Line 32, TABLE 3, delete "1,4-DPHCH" and insert -- di (2-propylheptyl)cyclohexane-1,4-dicarboxylate --

Column 11, Line 32, TABLE 3, delete "1,4-DINCH" and insert -- di (isononyl)cyclohexane-1,4-dicarboxylate --

Column 11, Line 32, TABLE 3, delete "1,4-DEHCH" and insert -- di (2-ethylhexyl)cyclohexane-1,4-dicarboxylate --

Column 11, Line 32, TABLE 3, delete "1,4-DPHCH" and insert -- di (2-propylheptyl)cyclohexane-1,4-dicarboxylate --

Column 12, Line 19, TABLE 4, delete "1,4-DINCH" and insert -- di (isononyl)cyclohexane-1,4-dicarboxylate --

Column 12, Line 19, TABLE 4, delete "1,4-DEHCH" and
insert -- di (2-ethylhexyl)cyclohexane-1,4-dicarboxylate --

Column 12, Line 19, TABLE 4, delete "1,4-DPHCH" and
insert -- di (2-propylheptyl)cyclohexane-1,4-dicarboxylate --

Column 12, Line 22, TABLE 4, delete "1,4-DINCH" and
insert -- di (isononyl)cyclohexane-1,4-dicarboxylate --

Column 12, Line 22, TABLE 4, delete "1,4-DEHCH" and
insert -- di (2-ethylhexyl)cyclohexane-1,4-dicarboxylate --

Column 12, Line 22, TABLE 4, delete "1,4-DPHCH" and
insert -- di (2-propylheptyl)cyclohexane-1,4-dicarboxylate --

Column 12, Line 60, TABLE 5, delete "1,4-DINCH" and
insert -- di (isononyl)cyclohexane-1,4-dicarboxylate --

Column 12, Line 62, TABLE 5, delete "1,4-DEHCH" and
insert -- di (2-ethylhexyl)cyclohexane-1,4-dicarboxylate --

Column 12, Line 64, TABLE 5, delete "1,4-DPHCH" and
insert -- di (2-propylheptyl)cyclohexane-1,4-dicarboxylate --

Column 13, Line 4, TABLE 5-continued, delete "1,4-DINCH" and
insert -- di (isononyl)cyclohexane-1,4-dicarboxylate --

Column 13, Line 6, TABLE 5-continued, delete "1,4-DEHCH" and
insert -- di (2-ethylhexyl)cyclohexane-1,4-dicarboxylate --

Column 13, Line 8, TABLE 5-continued, delete "1,4-DPHCH" and
insert -- di (2-propylheptyl)cyclohexane-1,4-dicarboxylate --

Column 13, Line 26, TABLE 6, delete "1,4-DINCH" and
insert -- di (isononyl)cyclohexane-1,4-dicarboxylate --

Column 13, Line 26, TABLE 6, delete "1,4-DEHCH" and
insert -- di (2-ethylhexyl)cyclohexane-1,4-dicarboxylate --

Column 13, Line 26, TABLE 6, delete "1,4-DPHCH" and
insert -- di (2-propylheptyl)cyclohexane-1,4-dicarboxylate --

Column 13, Line 26, TABLE 6, delete "1,4-DINCH" and
insert -- di (isononyl)cyclohexane-1,4-dicarboxylate --

CERTIFICATE OF CORRECTION (continued)
U.S. Pat. No. 8,299,292 B2

Column 13, Line 26, TABLE 6, delete "1,4-DEHCH" and insert -- di (2-ethylhexyl)cyclohexane-1,4-dicarboxylate --

Column 13, Line 26, TABLE 6, delete "1,4-DPHCH" and insert -- di (2-propylheptyl)cyclohexane-1,4-dicarboxylate --

Fig. 4

|  | cis 81%, trans 19% | cis 3%, trans 97% |  |
|---|---|---|---|
| Ex. 4<br><br>di(isononyl)cyclohexane-1,4-dicarboxylate | | | Comp. Ex. 4<br><br>di(isononyl)cyclohexane-1,4-dicarboxylate |
| Ex. 5<br><br>di(2-ethylhexyl)-cyclohexane-1,4-dicarboxylate | | | Comp. Ex. 5<br><br>di(2-ethylhexyl)-cyclohexane-1,4-dicarboxylate |
| Ex. 6<br><br>di(2-propylheptyl)-cyclohexane-1,4-dicarboxylate | | | Comp. Ex. 6<br><br>di(2-propylheptyl)-cyclohexane-1,4-dicarboxylate |